(12) United States Patent
Bolckmans et al.

(10) Patent No.: US 8,957,279 B2
(45) Date of Patent: *Feb. 17, 2015

(54) MITE COMPOSITION COMPRISING GLYCYPHAGIDAE AND PHYTOSEIID MITES, USE THEREOF, METHOD FOR REARING A PHYTOSEIID PREDATORY MITE, REARING SYSTEM FOR REARING SAID PHYTOSEIID PREDATORY MITE AND METHODS FOR BIOLOGICAL PEST CONTROL ON A CROP

(75) Inventors: Karel Jozef Florent Bolckmans, Wortel (BE); Yvonne Maria Van Houten, Delft (NL); Adelmar Emmanuel Van Baal, Delft (NL); Marisa Castagnoli, Florence (IT); Roberto Nannelli, Florence (IT); Sauro Simoni, Florence (IT)

(73) Assignee: Koppert B.V., Berkel en Rodenrijs (NL)

( * ) Notice: Subject to any disclaimer, the term of this patent is extended or adjusted under 35 U.S.C. 154(b) by 1114 days.

This patent is subject to a terminal disclaimer.

(21) Appl. No.: 12/158,447

(22) PCT Filed: Dec. 29, 2005

(86) PCT No.: PCT/NL2005/000899
§ 371 (c)(1),
(2), (4) Date: Oct. 28, 2008

(87) PCT Pub. No.: WO2007/075081
PCT Pub. Date: Jul. 5, 2007

(65) Prior Publication Data
US 2009/0205057 A1    Aug. 13, 2009

(51) Int. Cl.
*A01K 67/033* (2006.01)
*A01K 1/00* (2006.01)
*A01K 29/00* (2006.01)

(52) U.S. Cl.
CPC .................................. *A01K 67/033* (2013.01)
USPC .............................................. 800/8; 119/6.5

(58) Field of Classification Search
USPC .............................................. 800/8; 119/6.5
See application file for complete search history.

(56) References Cited

U.S. PATENT DOCUMENTS

| 4,646,683 | A | 3/1987 | Maedgen, Jr. |
| 6,129,935 | A | 10/2000 | White et al. |
| 8,097,248 | B2 * | 1/2012 | Bolckmans et al. ......... 424/93.7 |
| 2005/0178337 | A1 | 8/2005 | Wright |

FOREIGN PATENT DOCUMENTS

| CN | 14440646 | 9/2003 |
| GB | 2168680 | 6/1986 |
| GB | 2393890 | 4/2004 |
| JP | 03108433 A | 5/1991 |
| JP | 08040814 | 2/1996 |
| WO | 2006/057552 A1 | 6/2006 |
| WO | 2006/071107 A | 7/2006 |

OTHER PUBLICATIONS

Croft et al, Exp. & App. Acarol. 22:467-480, 1998.*
Colloff, Dust Mites, CSIRO Publishing, 2009; pp. 3-19.*
Palevsky et al., "Identification and evaluation of potential predators of the citrus rust mite, phyllocoptruta oleivora, in Israël" Systematic and Applied Acarology vol. 8, pp. 39-48 (2003).
Ramakers et al., "Manipulation of *Phytoseiid* thrips predators in the absence of thrips" IOBC/WPRS Bull. 13(5): 169-172 (1990).
Ramakers et al., "Start of commercial production and introduction of *Amblyseius* mckenziei Sch. & Pr. (Acarina: Phytoseiidae) for the control of Thirps tabaci lind. (Thysanoptera: Thripidae) in glasshouses" Mededelingen Faculteit Landbouwwetenschappen Rijksuniversiteit Gent vol. 47 No. 2, pp. 541-545 (1982).
Ramakers et al., "Mass production and introduction of *Amblyseius* mckenziei and A. cucumeris" IOBC WPRS Bulletin vol. 6, No. 3, 1983, pp. 203-206 (1983).
Ramakers et al., "Large scale introductions of *Phytoseiid* predators to control thrips on cucumber" Med. Fac. Landbouww. Rijksuniv. Gent vol. 54 No. 3a, pp. 923-929 (1989).
Rasmy et al., "A new diet for reproduction of two predaceous mites *Amblyseius* gossipi and agistemus exsertus [acari: Phytoseiidae, stigmaeidae]" Entomophaga vol. 32 No. 3 pp. 277-280 (1987).
Sampson C., "The commercial development of an *Amblyseius* cucumeris controlled release method for the control of *Frankliniella occidentalis* in protected crops" The 1998 Brighton Conference—Pests and diseases, vol. 5B-4, 1998, pp. 409-416 (1998).
Galun et al., Meeting—The 10th conference of the entomological society of Israël—Agricultural Entomology (several articles)ARO—The volcani Center, Bet. Dagan, Israël; 27pp. (1997).
Solomon et al., "Rearing acaroid mites" Acarologia, fasc. H.S. 1964 (C.R.Ier Congres Int. D'Acarologie, Fort Collins, Col., U.S.A. (1963).
Swirski et al., "Laboratory studies on the feeding and development and reproduction of the predaceous mites *Amblyseius* rubini, Swirski and Amitai and *Amblyseius swirskii*, Athias on various food substances" Israel Journal of Agricultural Resea vol. 17, No. 2, pp. 101-119 (1967).
Teich Y., "Mites of the family Phytoseiidae as predators of the tabacco whitefly, *Bemisia tabaci*, Gennadius" Israel Journal of Agricultural Resea vol. 16, No. 3, pp. 141-142 (1966).

(Continued)

*Primary Examiner* — Kevin Hill
(74) *Attorney, Agent, or Firm* — Bret E. Field; Bozicevic, Field & Francis LLP

(57) ABSTRACT

The present invention relates to a novel mite composition comprising a population of a phytoseiid predatory mite species and a factitious host population comprising a species selected from the Glycyphagidae, which may be employed for rearing said phytoseiid predatory mite species or for releasing the phytoseiid predatory mite species in a crop. According to further aspects the invention relates to a method for rearing a phytoseiid predatory mite species, to the use of the mite composition and to a method for biological pest control in a crop, which employ the mite composition.

27 Claims, 4 Drawing Sheets

(56) References Cited

OTHER PUBLICATIONS

Treat, A.E., "Mites of moths and butterflies" Cornell University Press, Ithaca and London, pp. 272-293 (1975).

Van Rijn et al., "Pollen availability and its effect on the maintenance of polulations of *Amblyseius* cucumeris, a predator of thrips" Med. Fac. Landbouww. Rijksuniv. Gent. 55: 335-341 (1990).

Vanninen et al., "Performance of *Neoseiulus cucumeris* as a biocontrol agent of the Western Flower Thrips in cut roses" Bulletin of OILB/SROP 25:1, 289-292 (2002).

Wahab et al., "Mites associated with vegetable and ornamental plants in lower Egypt äcarina parasitiformes acariformes" Database Biosis Online! Biosciences information service, Philadelphia, PA, US—Database accession No. PREV197865057938, abstract, & Bulletin de la societe entomologique D'Egypte, vol. 58, 1974, pp. 359-366, ISSN: 0373-3289 (1974).

Zdarkova E., "Section 4—Mites as pests of stored products. 14.1. Application of the bio-preparation 'cheyletin' in empty stores" Modern Acarology, Eds. Dusabeck & Bukva, vol. 1, pp. 607-610 (1991).

Zdarkova et al., "Space requirements of Cheyletus eruditus (Schrank) and Cheyletus malaccensis, Oudemans(Acarina, *Cheyletidae*)" Advances in Stored Product Protection, Eds. Credland, P.F. et al Proceedings of the VIII IWSCPP, pp. 183-185 (2002).

Zdarkova et al., "The effects of physical factors on survival of stored food mites" Exp. Appl. Acarol. 17:197-204 (1993).

Zdarkova et al., "Compatibility of Cheyletus eruditus (Schrank) (Arari: *Cheyletidae*) and Cephalonomia tarsalis (Ashmead) (Hymenoptera: Bethylidae) in Biological Control of Stored Grain Pests" Plant Protect. Sci. vol. 39, No. 1 pp. 29-34 (2003).

Zhang et al., "Potential of *Amblyseius* cucumeris (Acari: Phytoseiidae) as a biocontrol agent against schizotetranychus nanjingensis in Fujian, China" Systematic and Applied Acarology Special Publications vol. 4, pp. 109-124 (2000).

Karg, W. "Progress in the use of predatory mites for biological control in greenhouses. Fortschritte bei der Anwendung von Raubmilben zur biologischen Schädlingsbekämpfung in Gewächshäusern" Gartenbau: Zeitschrift fuer den Gemuesebau, Obstbau und Zierpflanzenbau der D.D.R. Voortz. Van : Deutsche Gartenbau Voortg. Als Gartenbau, vol. 36, No. 2 pp. 44-46 (1989).

Abou-Awad B.A. et al. "Impact of two eriophyoid fig mites, *Aceria ficus* and rhyncaphytoptus ficifoliae, as prey on postembryonic development and oviposition rate of the predacious mite *Amblyseius swirskii*" Acarologia, vol. Xl fasc. 4 pp. 367-371 (1999).

Abou-Awad B.A. et al. "Environmental management and biological aspects of the two eriophyoid fig mites *Aceria ficus* (cotte) and rhyncaphytoptus ficifoliae Keifer in Egypt" Anz. Schädlingskunde / J. Pest Science vol. 73, pp. 5-12, Blackwell Wissenschafts-Verlag Berlin ISSN 1436-5693 US Copyright Clearance Center code statement 1436-5693/00/7301-0005 (2000).

A. Koike et al., "Phyto-Trap" NII electronic Library Service Jpn. J. Appl. Entomol. Zool. vol. 44 pp. 35-40 (1999).

A. Enkegaard "Newsletter on biological control in greenhouses—several articles (New *Phytoseiid* predators)" Sting vol. 26, Danish Institute of Agricultural Sciences (2004).

Beglyarov, et al. "The flour mite [*Acarus siro*] for mass breeding of *Phytoseiids*." Zashchita-Rastenii No. 10, p. 25 (1990).

Bennison et al., "Integrated control of *Frankliniella occidentalis* (Pergande) in UK cucumber crops-evaluation of a controlled release system of introducing *Amblyseius* cucumeris." Med. Fac. Landbouww. Rijksuniv. Gent, vol. 56, No. 2A, 1991, pp. 251-255 (1991).

Bennison et al., "Recent developments with integrated control of thrips on cucumber in the United Kingdom." International Organisation for Biological and Integrated Control of noxious animals and plants, Glasshouse pests SROP/WPRS BULL. XIII/5 1990, pp. 19-26 (1990).

Castagnoli et al., "Effect of long term feeding history on functional and numerical responses of *Neoseiulus californicus* (Acari, *Phytoseiidae*)" Experimental and Applied Acarology. vol. 23, pp. 217-234 (1999).

Chant et al., "A review of the subfamily Ablyseiinae Muma (Acari;Phytoseiidae) Part I. Neoseiulini new tribe" International Journal of Acarology vol. 29: pp. 3-46 (2003).

Chant et al., "A review of the subfamily Amblyseiinae Muma (Acari:Phytoseiidae) Part III. The tribe Amblyseiini Wainstein, subtribe Amblyseiina N. Subtribe" International Journal of Acarology vol. 30: pp. 171-228 (2004).

Chmielewski W., Morfologia, biologia I ekologia *Carpoglyphus lactis* (L. 1758) (Glycyphagidae, Acarina) Summary morphology, biology and ecology of *Carpoglyphus lactis* (L. 1758) (Glycyphagidae, acarina) p. 164-166; Prace Nauk. Inst. Ochrony Roslin 13 vol. 13, No. 2, 1971, pp. 63-166 (abstract) (1971).

Chmielewski W., "Wyniki badan morfologicznych, biologicznych I ekologicznych nad rortoczkiem suszowym—*Carpoglyphus lactis*" Prace Nauk. Inst. Ochrony Roslin vol. 13, No. 1, 1971, pp. 87-106 (1971).

Chmielewski W., "Bionomics of *Carpoglyphus lactis* (Acari: Carpoglyphidae) on honey" in Bruin et al. (eds.) Ecology and evolution of Acari: 423-424 (1999).

Conjin et al., "Biological control of the bulb mite, Rhizoglyphus robini, by the predatory mite *Hypoaspis aculeifer*, on lilies: Implementation in practice" Acta Horticluturae vol. 430, pp. 619-624 (1997).

Karg et al., "Advantages of oligophagous predatory mites for biological control" Institute of plant protection Kleinmachnow, near Berlin GDR (1987).

El Halawany et al., "Mites inhabiting date palms" Plant Protection Research Institute, Dokki, pp. 366-371 (2000).

Ei-Laithy et al, "Life table parameters of the two *Phytoseiid* predators, *Amblyseius* scutalis (Athias-Henriot) and A. swirskii A.-H. (Acari, Phytoseiidae) in Egypt" J. Appl. Ent. 113 pp. 8-12 Verlag Paul Parey, Hamburg and Berlin ISSN 0931-2048 (1992).

Ei-Sherif et al., "Laboratory studies on Developmental and Oviposition Rates of *Amblyseius* Swirskii A.-H. (Acari: Phytoseiidae) Fed on *Tyrophagous putrescentiae* (Schrank) (Acari: Acaridea)" Arab Journal of Biotechnology vol. 2 No. 2 pp. 121-126 (1999).

Gerling et al., "Biological control of *Bemisia tabaci* using predators and parasitoids" Crop Protection vol. 20 pp. 779-799 (2001).

Gerson et al., "Mites (Acari) for Pest Control" Blackwell Science, Department of Entomology, Faculty of Agricultural Food and Environmental Sciences, Hebrew university, Rehovot, Israel / Systematic Entomology Laboratory, US Department of Agriculture, Agricultural Research Service, Beltsville, MD, USA Ingediend in KR dos 12: pp. 151-158 (2003).

Gilkeson L.A., "Mass rearing of *Phytoseiid* mites for testing and commercial application" Anderson, T.E. & Leppla, N.C.(eds.), Advances in insect rearing for research and pest management. Boulder, Colorado, Westview Press. pp. 489-506; (1992).

Gilkeson L.A., "Advances in insect rearing for research and pest management" Anderson, T.E. & Leppla, N.C. (Eds.) pp. 489-506 (1982).

Griffiths D.A., "A revision of the genus *Acarus* (Acaridae, Acarina)" Bull Brit. Mus. (nat. Hist.) (Zool), vol. 11, pp. 413-464 (1964).

Griffiths, D.A., "Some field habitats of mites of stored food products" Ann. Appl. Biol. vol. 48, pp. 134-144 (1960).

Houten et al., "Preselection of predatory mites to improve year-round biological control of western flower thrips in greenhouse crops" Entomologia Experimentalis et Applicata vol. 74, pp. 225-234 (1995).

Hughes A.M., "The mites of stored food and houses" 2nd ed. Ministry of Agriculture, Fisheries and Food, Technical Bulletin No. 9. His Majesty's Stationary Office, London, 287 pages; p. 26, 27, 41 & 43 (1976).

Jacobson, R.J., "Integrated pest management in cucumbers—prevention of establishment of *Frankliniella occidentalis* (pergande)" Med. Fac. Landbouww Univ. Gent 60/3a (1995).

Jarratt, J.H., "Stored-product pests" "Pest-Management Principles, pp. 61-67. Publication 2247 Mississippi State University Extension Service.http://msucares.com/pubs/publications/p2247ch7.pdr" (2001).

Kim, J. "Control of Thrips Using Predetory Mite" National Institute of Agricultural Science and Technology (2000).

(56) References Cited

OTHER PUBLICATIONS

Karg W., "Die ökologische Differenzierung der Raubmilbenarten der Überfamilie Phytoseioidea Karg (Acarina, Parasitiformes) The ecological differentiation of the predatory mite species of the superfamily Phytoseioidea Karg (acarina, Parasitiformes)" Zool. Jb. Syst. 116 31-46 VEB Gustav Fischer Verlag Jena (1989).

Kethley et al., "A terrestrial alicorhagiid mite (Acari: Acariformes)" Devonian of New York. Micropaleontology 35:367-373. (1989).

Knulle W., "Expression of a dispersal trait in a guild of mites colonizing transient habitats" Evolutionary Ecology 9: 341-353 (1995).

Lenteren et al., "Guidelines for quality control of commercially produced natural enemies" van Lenteren (ed.) Quality control and production of biological control agents—Theory and testing procedures. CABI Publishing, Wallingford: 265-303 (2003).

McMurtry et al., "Life-styles of *Phytoseiid* mites and their roles in biological control" Annual Review of Entomology 42: 291-321 (1997).

McMurtry et al., "Nutritional ecology of insects, mites, spiders, and related invertebrates: Nutritional ecology of *Phytoseiid* Mites" John Wiley & sons, new York, ISBN: 047180617X pp. 609-644 (1987).

Meshkov, Yu.L. "Guidelines for rearing and using *Neoseiiulus cucumeris* (formerly *Amblyseius* cucumeris) predatory mite against pellucid strawberry mite" Collection of guidelines for plants protection, S.-Petersburg pp. 87-92 (1998).

Momen et al., "Biology and feeding behaviour of the predatory mite, *Amblyseius swirskii* (Acari: Phytoseiidae)" National Research centre, plant protection department, Dokki Cairo, Egypt. Acarologia, t. XXXIV 34 fasc. 3 pp. 199-204 (1993).

Muma et al., "Phytoseiidae of Florida. Arthropods of Florida and neighbouring land areas" 6, Fla. Dept. Agr. Cons. Serv. Div. Plant Ind., Gainsville, 150 pages; p. 62, 100 (1970).

Nomikou et al., "*Phytoseiid* predators suppress populations of *Bemisia tabaci* on cucumber plants with alternative food" Experimental and Applied Acarology vol. 27: pp. 57-68 (2002).

Nomikou et al., "*Phytoseiid* predators of whiteflies fed and reproduce on non-prey food sources" Exp. Appl. Acarol. 31:15-26. (2003).

Nomikou et al., "*Phytoseiid* predator of whitefly feeds on plant tissue" Experimental and Applied Acarology vol. 31, pp. 27-36 Kluwer Academic Publishers, printed in the Netherlands (2003).

Nomikou et al., "*Phytoseiid* predators as potential biological control agents for *Bemisia tabaci*" Exp. Appl. Acarol. vol. 25. pp. 271-291; (2001).

Norton et al., "Oribatid mite fossils from a terrestrial Devonian deposit near Gilboa, New York" Journal of Paleontology 62:259-269. (1988).

Oudemans "10.4.2 *Neoseiulus* cucumeris Mites of Greenhouses Part III Beneficial Mites" ; Chapter 10 *Phytoseiid* Mites ; pp. 186-189 (n. d.).

Overmeer, W.P.J., "2.1.3.2. Alternative Prey and other food resources" Alternative prey and other food resources, p. 131-137. In Helle W, Sabelis MW, Spider mites, their biology, natural enemies and control vol. 1B. In Helle W, Sabel MW, Spider mites, Their biology, natural enemies and control vol. 1B. Amsterdam, Elsevier Science Publishers BV, Amsterdam (1995).

Rodriguez et al. Nutritional ecology of insects, mites, spiders, and related invertebrates. Nutritional Ecology of *Phytoseiid* Mites, Mar. 1987, 609-644, John Wiley & Sons, New York.

Ehara "Illustrations of the Miteas and Ticks in Japan" Zenkoku Noson Kyoiku Kyokai pp. 389 and 505-509, 1st Ed. published on Oct. 30, 1980.

Gerson et al., "Acarine Biocontrol agents—an illustrated key and manual" Chapman and Hall London pp. 24-35 (1990).

Gerson et al., "Mites (Acari) for Pest Control" Blackwell Science, Department of Entomology, Faculty of Agricultural Food and Environmental Sciences, Hebrew university, Rehovot, Israel / Systematic Entomology Laboratory, US Department of Agriculture, Agricultural Research Service, Beltsville, MD, USA pp. 173-218 (2003).

Hansen et al., "Possibilities and limitations of the use of *Amblyseius Mckenziei* Sch. & Pr. For biological control of thrips (Thrips tabaci Lind.) on glasshouse crops of cucumber" Department of Zoology, Danish Research Centre for plant protection, Lynby, Denmark pp. 145-150 (1985).

Parkinson C.L., "Culturing free-living astigmatid mites" Adas Slough Laboratory, Ministry of Agriculture Fisheries and Food, London Road, Slough, Berhshire (1992).

Zhang "10.4.2 *Neoseiulus cucumeris* Mites of Greenhouses Part III Beneficial Mites" ; Oudemans, Chapter 10 *Phytoseiid* Mites ; pp. 186-189 (2003).

Hughes, "The Mites of Stored Food and Houses", Technical Bulletin 9, Ministry of Agriculture, Fisheries and Food, 1977, pp. 133-186.

McMurtry & Rodriguez, "Nutritional Ecology of Insects, Mites, Spiders, and Related Invertebrates", Chapter 19, "Nutritional Ecology of *Phytoseiid* Mites", 1987, John Wiley & Sons, Inc., pp. 609-644.

\* cited by examiner

Figure 1

List of *Glycyphagidae* species and their genus name as referred in :Hughes, A.M., 1977, The mites of stored food and houses. Ministry of Agriculture, Fisheries and Food, Technical Bulletin No. 9: pp 133-186.

Class: Arachnidae
Subclass: Acari
Order: Astigmata Canestrini, 1891
Family: Glycyphagidae Berlese, 1887
Subfamilies, Genera and Species:
    Ctenoglyphinae Zachvatkin, 1941
        Diamesoglyphus Zachvatkin, 1941
            D. intermedius (Canestrini, 1888)
        Ctenoglyphus Berlese, 1884
            C. plumiger (Koch, 1835)
            C. Cnestrinii (Armanelli, 1887)
            C. palmifer (Fumouze and Robin, 1868)
    Glycyphaginae Zachvatkin, 1941
        Blomia Oudemans, 1928
            B. freemani (Hughes, 1948)
        Glycyphagus Hering, 1938 s.str.
            G. ornatus (Kramer, 1881)
            G. bicaudatus (Hughes, 1961)
            G. privatus (Oudemans, 1903)
            G. domesticus (De Geer, 1778)
        Lepidoglyphus Zachvatkin, 1936
            L. michaeli (Oudemans, 1903)
            L. fustifer (Oudemans, 1903)
            L. destructor (Schrank, 1781)
        Austroglycyphagus (Fain and Lowry, 1974)
            A. geniculatus (Vitzthum, 1919)

Figure 1 continued

Aëroglyphinae Zachvatkin, 1941
        Aëroglyphus Zachvatkin, 1941
            A. robustus (Cooreman, 1959)
    Labidophorinae Zachvatkin, 1941
        Gohieria Oudemans, 1939
            G. fusca (Oudemans, 1902)
    Nycteriglyphinae Fain, 1963
        Coproglyphus Türk and Türk, 1957
            C. stammeri (Türk and Türk, 1957)

Figure 2

List of phytoseiid species and their genus name as referred in : Moraes, G.J. de, J.A. McMurtry, H.A. Denmark & C.B. Campos (2004). A revised catalog of the mite family Phytoseiidae. Magnolia Press Auckland New Zealand 494 pp.

Family : PHYTOSEIIDAE Berlese
    Subfamily : AMBLYSEIINAE Muma
        Genus : Amblyseius Berlese
            Amblyseius andersoni (Chant, 1957)
            Amblyseius swirskii Athias-Henriot, 1962, (Chant and McMurtry), 2004, (= Typhlodromips swirskii (Athias-Henriot), 1962, Moraes et al., 2004)
            Amblyseius largoensis (Muma, 1955)
        Genus : Euseius Wainstein
            Euseius finlandicus (Oudemans, 1915)
            Euseius hibisci (Chant, 1959)
            Euseius ovalis (Evans, 1953)
            Euseius victoriensis (Womersley, 1954)
            Euseius stipulatus ((Athias-Henriot, 1960)
            Euseius scutalis (Athias-Henriot, 1958)
            Euseius tularensis Congdon
            Euseius addoensis (van der Merwe & Ryke, 1964)
            Euseius citri (van der Merwe & Ryke, 1964)
            Euseius concordis (Chant, 1959)
            Euseius ho (De Leon, 1965)
        Genus : Neoseiulus Hughes
            Neoseiulus barkeri (Hughes, 1948)
            Neoseiulus californicus (McGregor, 1954)

Figure 2 continued

>                    Neoseiulus cucumeris (Oudemans, 1930)
>                    Neoseiulus longispinosus (Evans, 1952)
>                    Neoseiulus womersleyi (Schicha, 1975)
>                    Neoseiulus idaeus (Denmark & Muma, 1973)
>                    Neoseiulus fallacis (Garman, 1948)
>                    Neoseiulus anonymous (Cahnt & Baker, 1965)
>          Genus : Typhlodromalus Muma
>                    Typhlodromalus limonicus (Garman & McGregor, 1956)
>                    Typhlodromalus peregrinus (Muma, 1955a)
>                    Typhlodromalus arip (De Leon, 1967)
>          Genus : Typhlodromips De Leon
>                    Typhlodromips montdorensis (Schicha, 1979)
> Subfamily : TYPHLODROMINAE Scheuten
>          Genus : Galendromus Muma
>                    Galendromus occidentalis (Nesbitt, 1951)
>          Genus : Typhlodromus Scheuten
>                    Typhlodromus pyri (Scheuten, 1857)
>                    Typhlodromus doreenae (Schicha, 1987)
>                    Typhlodromus athiasae (Porath & Swirski, 1965)

MITE COMPOSITION COMPRISING *GLYCYPHAGIDAE* AND *PHYTOSEIID* MITES, USE THEREOF, METHOD FOR REARING A *PHYTOSEIID* PREDATORY MITE, REARING SYSTEM FOR REARING SAID *PHYTOSEIID* PREDATORY MITE AND METHODS FOR BIOLOGICAL PEST CONTROL ON A CROP

This invention according to a first aspect relates to a novel mite composition comprising at least one species from the Glycyphagidae and at least one phytoseiid mite species.

According to a second aspect the invention relates to a novel method for rearing a phytoseiid predatory mite species.

According to a third aspect the invention relates to a novel use of an Astigmatid mite species selected from the family of the Glycyphagidae as a factitious host, for rearing a phytoseiid predatory mite species.

According to a fourth aspect the invention relates to a novel rearing system for rearing a phytoseiid predatory mite species. According to a fifth aspect the invention relates to the use of the mite composition or the rearing system for the control of crop pests.

According to yet further aspects the invention relates to a method for biological pest control in a crop employing the mite composition according to the invention.

In the following description and claims the names of the phytoseiid mite subfamilies, genera and species is as referred to in de Moraes, G. J. et al., 2004, unless otherwise stated. In the following description and claims the names of the Glycyphagidae subfamilies, genera and species is as referred to in Hughes, A. M., 1977, unless otherwise stated. An overview of the referenced families, subfamilies, genera and species is provided in FIGS. 1 and 2.

Phytoseiid predatory mites (Phytoseiidae) are widely used for biological control of spider mites and *thrips* in greenhouse crops. The most important *thrips* species in greenhouse crops are Western Flower *Thrips* (*Frankliniella occidentalis*) and Onion *Thrips* (*Thrips tabaci*). They can be controlled with the predatory mites *Neoseiulus cucumeris* and *Neoseiulus barkeri* (Hansen, L. S. and Geyti, J., 1985; Ramakers, P. M. J. and van Lieburg, M. J., 1982; Ramakers, P. M. J., 1989; Sampson, C., 1998; and Jacobson, R. J., 1995) and *Iphiseius degenerans* (Ramakers, P. M. J. and Voet, S. J. P., 1996). In the absence of prey these species are able to establish, develop and maintain in crops which provide a continuous supply of pollen, such as sweet peppers (*Capsicum annuum* L.) and eggplants (*Solanum melogena*). Therefore they can be released preventively in these crops, before the suitable target pest prey is present. Also they are able to survive and continue to develop once the target pest has been controlled. The possibility for preventive releases is very important in order to obtain a robust biological control program. Excellent results are obtained with preventive release of predatory mites (because the prey can be controlled immediately when it enters the crop). In crops where pollen is not freely available, such as for example cucumbers and most ornamental crops, these phytoseiid mite species cannot be released preventively unless food is artificially provided. This can e.g. be done by dusting artificially collected plant pollen on the crop.

Alternatively, or in addition to this, this could also be done by releasing the target pest prey before or together with releasing the phytoseiid predatory mites. This method, known as pest-in-first, involves obvious risks of introducing the pest and requires a lot of experience. The best known example of pest-in-first is the release of two-spotted spider mites (*Tetranychus urticae*) together or prior to the release of the phytoseiid mite *Phytoseiulus persimilis*.

In the case of *Neoseiulus cucumeris* alternatively a controlled release rearing system (as disclosed by Sampson, C. (1998) or in GB2393890) can be used for preventive release of this phytoseiid mite species. This controlled release rearing system consists of a sachet with a compartment which contains a food mixture, consisting of bran, yeast and wheat germ; a population of the grain mite *Tyrophagus putrescentiae* and a population of the predatory mite *Neoseiulus cucumeris*. The grain mite *Tyrophagus putrescentiae* will reproduce and develop an active population on the food mixture and serves as a factitious host for the predatory mite population. The sachets are hung in the crop with suitable means, e.g. by means of a hook and will continuously release predatory mites over a period of 4 to 6 weeks.

In crops which provide a continuous supply of pollen or in case pest populations are already present, a slow-release sachet is not needed and the product can be applied on the crop as a loose material, comprising of suitable rearing medium with a population of the grain mite *Tyrophagus putrescentiae* and the phytoseiid *Neoseiulus cucumeris*.

Because *Neoseiulus cucumeris* has a rather weak numerical response to the presence of food, large quantities of predatory mites have to be released into a crop in order to have sufficient pest control. This is economically possible because *Neoseiulus cucumeris* can be economically reared in very large quantities on the grain mite *Tyrophagus putrescentiae*, which may be reared in sufficient amounts on the above described food mixture.

Although there are much more efficient predatory mites for *thrips* control with a higher predation rate and numerical response, such as *Typhlodromalus limonicus* and *Iphiseius degenerans*, *Neoseiulus cucumeris* is still the most commonly used species because it can easily be reared in very large quantities.

*Iphiseius degenerans* is mass-reared on Castor Bean Plants (*Ricinus communis* L., Euphorbiaceae) which provide a continuous supply of pollen on which the mites can develop large populations. Because of the large surface and high investment in greenhouses needed for growing the plants and because of the laborious harvesting techniques, the cost price of *Iphiseius degenerans* is very high compared to *Neoseiulus cucumeris*. Due to this high cost price growers can only release very low numbers, typically 1000-2000 predatory mites per hectare. Therefore, the application of *Iphiseius degenerans* is limited to peppers (*Capsicum annuum* L.), which provide sufficient pollen on which the predatory mites can develop a population, which is sufficient for pest control. Because only small numbers of mites can be released at the beginning of the growing season, it takes several months before the population of *Iphiseius degenerans* is at sufficient strength in a crop in order to be able to have a significant impact on *Thrips* pest populations.

Two-spotted Spider Mites (*Tetranychus urticae*) are successfully controlled in greenhouse and outdoor crops worldwide by releasing predatory mites. The most important species are *Phytoseiulus persimilis* (Hussey, N. W. and Scopes, N. E. A., 1985), which is the oldest mite which is commercially available for biological control and *Neoseiulus californicus* (Wei-Lan Ma and Laing, J. E., 1973). Both predatory mites are mass-reared on their natural host *Tetranychus urticae* on bean plants (*Phaseolus vulgaris*) in greenhouses. Castagnoli, M. and Simoni, S. (1999) have also described a method for mass-rearing *Neoseiulus californicus* on the House Dust Mite *Dermatophagoides farinae*. However, House Dust Mites (*Dermatophagoides farinae* and *Dermatophagoides pteronyssinus*) produce important allergens, implicated in allergic asthma, rhinitis, conjunctivitis and dermatitis. Therefore their use in controlled release rearing systems for releasing predatory mites in crops has disadvantages. Another disadvantage is that when House Dust Mites are used for mass-rearing purposes, extensive measures are necessary for worker protection. Scientific literature reports many predatory mites which are highly effective against damaging crop pest species such as white flies, *thrips*, spider mites, tarsonemid mites and eriophyid mites, but, due to the absence of an efficient and cost-effective mass-rearing system, only a few species are commercially available for biological pest control purposes.

Recent research has indicated the potential of the predatory mites *Amblyselus swirskii*, *Euseius ovalis*, *Euseius scutalis* and *Typhlodromalus limonicus* as very efficient biological control agents of *thrips* (*Thrips tabaci* and *Frankliniella occidentalis*) and whiteflies (*Trialeurodes vaporariorum* and *Bemisia tabaci*) (Nomikou, M., Janssen, A., Schraag, R. and Sabelis, M. W., 2001; Messelink, G. & Steenpaal, S. 2003; Messelink, G. 2004; Messelink, G. & Steenpaal, S. 2004; Bolckmans, K. & Moerman, M. 2004; Messelink, G. & Pijnakker, J. 2004; Teich, Y. 1966; Swirski, E. et al., 1967). However, the practical usability of these and other phytoseiid predatory mites as an augmentative biological control agent depends on the availability of a suitable method for mass-rearing there predatory mites.

To date only *Amblyseius swirskii* is commercially available for biological control of whiteflies. Recently this phytoseiid mite was introduced to the market by Koppert B. V. Commercial market introduction of *Amblyseius swirskii* was possible due to the development of a commercially feasible method for mass-rearing this predatory mite, which involves the use of *Carpoglyphus lactis* as a factitious host. This method is part of the subject matter of the pending non-prepublished international application NL2004/000930.

The reason, that only recently a predatory mite, which preys on white flies, has become commercially available, is probably because despite the known predation of predatory mites on whiteflies their usability as augmentative biological control agents against whiteflies has not been recognized in the art. In augmentative biological control, biological agents are released in a crop for the control of a pest.

Even more important, with the exception of the recently developed rearing system for *Amblyseius swirskii*, no economic mass-rearing systems, necessary for allowing the release of large numbers of predatory mites into a crop, which is of utmost importance for their usability as an augmentative biological control agent, are available in the art for predatory mite species, e.g. those which could potentially be efficacious against whiteflies or other crop pests.

Biological control of crop pests with predatory mites which can be economically reared in large quantities on a factitious host mite in a rearing medium would be very advantageous because such a rearing system uses a limited surface. Furthermore in such a system rearing of the predatory mite can be performed in controlled climate rooms. As such it does not require large investments in greenhouses and crops.

The prior art describes rearing of *Neoseiulus cucumeris* and *Neoseiulus barkeri* with the aid of a factitious host mite species from the genus *Tyrophagus*, in particular *Tyrophagus putrescentiae*, *Tyrophagus tropicus*, *Tyrophagus casei* (Sampson, C., 1998; Jacobson, R. J., 1995; Bennison, J. A. and R. Jacobson, 1991; Karg et al., 1987; and GB293890) and from the genus *Acarus*, in particular *Acarus siro* (Beglyarov et al., 1990) and *Acarus farris* (Hansen, L. S. and J. Geyti, 1985; Ramakers, P. M. J. and van Lieburg, M. J., 1982), which all belong to the family of the Acaridea.

The most common rearing host for *Neoseiulus cucumeris* is *Tyrophagus putrescentiae*. An important disadvantage of *Tyrophagus putrescentiae* is that it can cause plant damage to young plant leaves when it is present on crops, e.g. when used as a factitious host in slow release breeding sachets similar to that disclosed by (Sampson, C., 1998) or in GB293890. This is especially the case in cucumber crops during periods of high humidity especially if this is combined with a low light intensity.

Castagnoli et al. have also described the possibility of mass-rearing *Neoseiulus californicus* (Castagnoli, M. and S. Simoni, 1999) and *Neoseiulus cucumeris* (Castagnoli, M., 1989) on the House Dust Mite *Dermatophagoides farinae* as a factitious rearing host. However, House Dust Mites (*Dermatophagoides farinae* and *Dermatophagoides pteronyssinus*) produce important allergens, implicated in allergic asthma, rhinitis, conjunctivitis and dermatitis.

Therefore the traditional method for mass-rearing *Neoseiulus californicus* is on bean plants (*Phaseolus vulgaris*) infested with two-spotted spider mites (*Tetranychus urticae*) or pacific mites (*Tetranychus pacificus*) in greenhouses which results in a rather high cost price. Due to the cost price of mites which are reared in this system, only relatively low numbers can be released to control pests in a crop. Development of a mas-rearing method with a factitious host which can be reared on a suitable medium would result in a much lower cost price and therefore allow the release of much higher numbers as biocontrol agents in crops. The factious hosts, which are known in the prior art, such as *Tyrophagus* spp., *Acarus* spp. are only suitable for mass-rearing a limited number of phytoseiid mite species. For example the phytoseiid mites *N. californicus* and *N. fallacis* cannot be reared efficiently on *Tyrophagus putrescentiae* and *Acarus siro*.

Thus there is a need in the art for additional factitious hosts which can be used for mass rearing beneficial mites, such as predatory mites. Especially for rearing of *Amblyseius swirskii, Neoseiulus fallacis, Neoseiulus californicus, Typhlodromips montdorensis, Neoseiulus womersleyi, Euseius ovalis* or *Euseius scutalis*. For many phytoseiid predatory mite species only rearing on plant pollen has been disclosed in literature.

Rearing on pollen necessitates either large greenhouse areas for the production of plants such as Castor Bean Plants (*Ricinus communis*) to obtain sufficient pollen, or collecting suitable plant pollen such as from Cattail (*Typha* spp.) or Oak (*Quercus* spp.) outdoors. Collecting plant pollen outdoors is very labour intensive and therefore expensive and only limited quantities can be collected. Honeybee collected plant pollen is unsuitable for rearing predatory mites.

For *A. swirskii* mite rearing has only been disclosed in the art using pollen (Messelink, G. & Pijnakker, J. 2004) or eggs from the lepidopterans *Corcyra cephalonica* or *Ephestia kuehniella* (Romeih, A. H. M. et al., 2004).

Rearing on lepidopteran eggs requires large investments in production facilities and thus is very expensive. Also, rearing on lepidopteran eggs is not suitable for several mite species such as for example *Neoseiulus californicus* and *Neoseiulus fallacis*.

In addition to this mass-rearing of *Amblyseius swirskii* on the factitious host *Carpoglyphus lactis* is now known. In order to fully comply with the demands of the market, additional factitious hosts are necessary.

SUMMARY OF THE INVENTION

It has now been found that Astigmatid mite species from the family of the Glycyphagidae may be used as a factitious host for a great number of phytoseiid predatory mite species.

BRIEF DESCRIPTION OF THE DRAWINGS

FIG. 1 provides a list of Glycyphagidae species and their genus name.

FIG. 2 provides a list of Phtoseiid species and their genus name.

DETAILED DESCRIPTION

Thus according to a first aspect the invention relates to a mite composition comprising a rearing population of a phytoseiid predatory mite species and a factitious host population comprising at least one species selected from the family of the Glycyphagidae.

The mite composition according to the invention preferably comprises a limited number of different species. It will be understood that the mite composition will comprise at least two distict species, the phytoseiid mite and the factitious host selected from the Glycyphagidae. It is however possible that the mite composition comprises more than two species e.g. by comprising more than one, such as two or three factitious host species or by comprising more that one, such as two or three, phytoseiid mite species. It is however less preferred that the mite composition comprises more that one phytoseiid mite species, as intraguild predation may occur.

The phytoseiid predatory mite species which are most likely to be able to feed on species selected from the Glycyphagidae and in particular *Lepidoglyphus destructor* or *Glycyphagus domesticus* are oligophagous phytoseiid predatory mite species. An oligophagous phytoseiid predatory mite species is a phytoseiid predatory mite species which is able to use at least a few different prey species as a food source for its population development (reproduction and complete development of its individuals from egg to sexually mature adult). As such the term oligophagous predatory mite species in this specification includes a polyphagous mite species, being a predatory mite which can use a great number of prey species as a food source for its reproduction and complete development. Thus the term oligophagous predatory mite species is to be understood to mean a non-monophagous predatory mite species such as predatory mite species from the genus *Phytoseiulus* which have a very narrow host range which is mostly limited to the genus *Tetranychus*.

Factitious host species and factitious prey species are species which inhabit a different natural habitat then the phytoseiid predatory mite, but nevertheless one or more life stages of the factitious host or factitious prey are suitable prey for at least one life stage of the phytoseiid predatory mite. Because factitious hosts and factitious preys inhabit a different natural habitat than phytoseiid predatory mites, whose natural habitat is the phyllosphere of plants, phytoseiids normally do not feed on them in nature. The phytoseiid predatory mite has the ability to reproduce and develop efficiently from egg to sexually mature adult when feeding upon a diet of the factitious host such that the number of individuals in the rearing population of the phytoseiid mite can grow with at least 50%, preferably 75%, more preferably 100% in 7 days (T=25° C.; RH=80% feeding ad libidum).

In contrast to this, a factitious prey is a prey on which a phytoseiid mite species may be able to prey, however development of egg to sexually mature adult is not efficient. A very low fecundity and high mortality is observed during development from egg to adult, resulting in a population increase of less than 50% in 7 days under mass-rearing conditions. As such, when feeding on a diet consisting solely of a factitious prey, a rearing population of a phytoseiid predatory mite will not be able to increase the number of its individuals by at least 50%, in 7 days time (T=25° C.; RH=80%, feeding ad libidum), which is considered a minimum requirement for commercial mass-rearing.

Phytoseiid predatory mites have their natural habitat on plants where they prey on pest organisms (insects and mites). They may be isolated from their natural habitats as described by de Moraes et al., 2004.

Glycyphagidae are described by Hughes, A. M. (1977). Based on the disclosure of this document the skilled person will be able to isolate specific species from this family from their natural habitat. As described by Hughes, A. M. (1977) Glycyphagidae are associated with insects or small mammals or nests of small mammals and social insects such as bees. They are typically associated with houses, stables and with storage or processing of dried food products such as granaries and flour mills. In houses they can be found in materials such as floor dust, damp and mouldy wall paper, felt, dried animal skins, storage of stored food products and in upholstery made from processed plant fibres. In animal stables they can be found in materials such as hay, straw, floor dust, dried animal food (pellets or flour), stored grains and poultry droppings. Typical stored food products on which Glycyphagidae can be found are flour, grains, cereals, cheese, ham, dried fish, dried yeast, seeds and dried fruit.

Thus the composition according to the invention provides a new association of mites, which does not occur naturally, as the phytoseiid predatory mites inhabit a different habitat than the Glycyphagidae.

Dyadechko, N. P. and Chizhik, R. I. (1972) disclose experiments wherein *Typhlodromus aberrans* (currently known as *Campynodromus aberrans* (Oudemans 1930)) is collected in felt bands during Autumn with the goal to release them in other orchards in the next spring. Apart from *Typhlodromus aberrans*, the spider mite *Tetranychus telarius* is collected. Predation of *Typhlodromus aberrans* on *Tetranychus telarius* is described. It is described that after fully having eradicated the spider mite *Tetranychus telarius* from the felt bands *Typhlodromus aberrans* fed on a non-specified species of *Glycyphagus* which was present in the felt bands. No information is given about reproduction of *T. aberrans* on the unspecified *Glycyphagus* species, only about predation.

The composition according to the invention is not only suitable for mass-rearing of a phytoseiid predatory mite. As it also comprises mobile preying life stages of a phytoseiid predatory mite, or life stages which can develop into these mobile life stages, it can also be employed as a biological crop protection agent.

In a preferred embodiment the composition comprises a carrier for the individuals of the populations. The carrier can be any solid material which is suitable to provide a carrier surface to the individuals. Preferably the carrier provides a porous medium, which allows exchanges of metabolic gases and heat produced by the mite populations. Examples of suitable carriers are plant materials such as (wheat) bran, buckwheat husks, rice husks, saw dust, corn cob grits etcetera.

It is further preferred if a food substance suitable for the development of the factitious host population is added to the composition. Alternatively the carrier itself may comprise a suitable food substance. A suitable food substance may be similar to that described by Parkinson, C. L., 1992; Solomon, M. E. & Cunnington, A. M., 1963; Chmielewski, W, 1971a; Chmielewski, W, 1971b or GB2393890.

According to a preferred embodiment of the composition the phytoseiid predatory mite is selected from:

- the subfamily of the Amblyseiinae, such as from the Genus *Amblyseius*, e.g. *Amblyseius andersoni*, *Amblyseius swirskii* or *Amblyseius largoensis*, from the genus *Euseius* e.g. *Euseius finlandicus*, *Euseius hibisci*, *Euseius ovalis*, *Euseius victoriensis*, *Euseius stipulatus*, *Euseius scutalis*, *Euseius tularensis*, *Euseius addoensis*, *Euseius concordis*, *Euseius ho* or *Euseius citri*, from the genus *Neoseiulus* e.g. *Neoseiulus barkeri*, *Neoseiulus californicus*, *Neoseiulus cucumeris*, *Neoseiulus longispinosus*, *Neoseiulus womersleyi*, *Neoseiulus idaeus*, *Neoseiulus anonymus* or *Neoseiulus fallacis*, from the genus *Typhlodromalus* e.g. *Typhlodromalus limonicus*, *Typhlodromalus aripo* or *Typhlodromalus peregrinus* from the genus *Typhlodromips* e.g. *Typhlodromips montdorensis*;
- the subfamily of the Typhlodrominae, such as from the genus *Galendromus* e.g. *Galendromus occidentalis*, from the genus *Typhlodromus* e.g. *Typhlodromus pyri*, *Typhlodromus doreenae* or *Typhlodromus athiasae*. These phytoseiid predatory mite species may be considered as being oligophagous predatory mite species.

The phytoseiid predatory mite according to a preferred embodiment of the invention is selected from the subfamily Amblyseiinae as described by De Moraes et al., 2004. In a further preferred embodiment the phytoseiid predatory mite is selected as *Amblyselus swirskii*, *Neoseiulus fallacis*, *Neoseiulus californicus*, *Typhlodromips montdorensis*, *Neoseiulus womersleyi*, *Euseius ovalis* or *Euseius scutalis*. For these species economic mass-rearing on a factitious host mite has not been disclosed in the art, with the exception of *A. swirskii* and *N. californicus*.

Mass-rearing of *Neoseiulus californicus* on *Dermatophagoides farinae* has been described in the art (Castagnoli, M. and Simoni, S. (1999)) as discussed above. However, this is associated with problems relating to the allergens carried by Dermatophagoidea. Mass-rearing of this species on *Tetranychus urticae* or *Tetranychus pacificus* on bean plants (*Phaseolus vulgaris*) in greenhouses or outdoors has also been described in the art (Hendrickson, R. M., Jr., (1980); Glasshouse Crops Research Institute, UK. (1976)), as discussed above. However, this is associated with high investments in greenhouses and high input of labour, material and energy.

Commercial mass-rearing of *Amblyseius swirskii* has only been publicly disclosed with the use of the factitious host *Carpoglyphus lactis* as a factitious host. It will be beneficial to provide additional factitious hosts for the mass-rearing of this predatory mite.

For *Typhlodronmips montdorensis*, *Neoseiulus womersleyi*, *Euseius ovalis* and *Euseius scutalis* laboratory-scale rearing on plant pollen has been disclosed. However, commercial mass-rearing on pollen is expensive and thus not economically favourable.

*Neoseiulus fallacis* is commercially available. However, this predatory mite is mass-reared on its natural prey, which involves large investments.

The present invention now for the first time discloses a mite composition, comprising a species from the family of the Glycyphagidae as a factitious host, which can be used for economic rearing of these and other phytoseiid predatory mite species. Making it possible to use them as an augmentative biological pest control agent.

It should however be understood that in certain embodiments of the invention the phytoseiid predatory mite species is selected from a species other than those, which are particularly preferred.

Differences in acceptance of the factitious host may be observed between different strains of the phytoseiid predatory mite species. Furthermore, it might be possible to breed a strain, which is adapted to a specific factitious host by selective breeding.

In this specification the term rearing must be understood to include the propagation and increase of a population by means of sexual reproduction.

A rearing population may comprise sexually mature adults from both sexes, and/or individuals of both sexes of other life stages, e.g. eggs and/or nymphs, which can mature to sexually mature adults. Alternative the rearing population may comprise one or more fertilized females. In essence the rearing population is capable of increasing the number of its individuals by means of sexual reproduction.

Preferably the factitious host population is a rearing population, as defined above, such that it may sustain or even develop itself to a certain degree. If the factitious host is provided as a rearing population, preferably a food substance for the factitious host is also provided. The food substance may be similar to a food substance as disclosed in Solomon, M. E. and Cunnington, A. M., 1963; Parkinson, C. L., 1992; Ramakers, P. M. J. and van Lieburg, M. J., 1982; GB2393890. The factitious host is preferably selected from the subfamily Ctenoglyphinae, such as from the genus *Diamesoglyphus* e.g. *D. intermedius* or from the genus *Ctenoglyphus*, e.g. *C. plumiger*, *C. canestrinii*, *C. palmifer*; the subfamily Glycyphaginae, such as from the genus *Blomia*, e.g. *B. freemani* or from the genus *Glycyphagus*, e.g. *G. ornatus*, *G. bicaudatus*, *G. privatus*, *G. domesticus*, or from the genus *Lepidoglyphus* e.g. *L. michaeli*, *L. fustifer*, *L. destructor*, or from the genus *Austroglycyphagus*, e.g. *A. geniculatus*; from the subfamily Aëroglyphinae, such as from the genus *Aëroglyphus*, e.g. *A. robustus*; from the subfamily Labidophorinae, such as from the genus *Gohieria*, e.g. *G. fusca*; or from the subfamily Nycteriglyphinae such as from the genus *Coproglyphus*, e.g. *C. Stammeri*, and more preferably is selected from the subfamily Glycyphaginae, more preferably from the genus *Glycyphagus* or the genus *Lepidoglyphus* most preferably selected from *G. domesticus* or *L. destructor*. Contrary to *Tyrophagus putrescentiae*, for the Glycyphagidae and in particular *Lepidoglyphus destructor* and *Glycyphagus domesticus* no damage to crops has been observed in comparative field trials. Therefore, a factitious host from this selection will have benefits when the composition according to the invention is used for crop protection in such a way that individuals of the factitious host population may come in contact with the crop e.g. when applied directly on or in the vicinity of the crop or when used in slow/controlled/sustained release sachets.

A further benefit of the Glycyphagidae and particularly of *Lepidoglyphus destructor* and *Glycyphagus domesticus* is that they are considered to be cosmopolitan species. As such international trade of products comprising one of them will encounter less regulatory restrictions as is encountered in many countries for foreign species.

A further benefit of the Glycyphagidae and in particular *Lepidoglyphus destructor* and *Glycyphagus domesticus* is that they can be used to commercially mass-rear certain phytoseiid predatory mite species which cannot be reared on *Tyrophagus* spp. or *Acarus* spp., such as *Neoseiulus fallacis* and *Neoseiulus californicus*.

Also it has been found that *Lepidoglyphus destructor* and *Glycyphagus domesticus* are in particular suitable factitious hosts for *Neoseiulus californicus* and for *Neoseiulus fallacis* as these predators can feed on multiple life stages and under certain circumstances all life stages of these hosts.

In the composition the number of individuals of the phytoseiid predatory mite species relative to the number of individuals of the factitious host may be from about 1000:1 to 1:20, such as about 100:1 to 1:20 e.g. 1:1 to 1:10, preferably about 1:4, 1:5 or 1:7.

The relative numbers may depend on the specific intended use of the composition and/or the stage of development of phytoseiid mite population on the factitious host. In general compositions wherein individuals of the factitious host are present in excess to the individuals of the phytoseiid mite are preferred for rearing of the phytoseiid mite species, so that sufficient prey is provided to the phytoseiid mite. However, as the phytoseiid mite population will increase while preying on the factitious host, the relative number of individuals of the phytoseiid mite species will increase.

A composition comprising a high relative number of the phytoseiid predatory mite may be formed from a composition comprising a smaller relative number and allowing the rearing population of the phytoseiid predatory mite to develop by preying on the factitious host. Alternatively a composition comprising a small relative number of the phytoseiid predatory mite can be formed by mixing a composition comprising a higher relative number with a composition comprising a smaller relative number, including a composition comprising solely the factitious host, optionally in combination with the carrier and/or a food substance suitable for the factitious host.

According to a preferred embodiment the mite composition comprises a further nutritional source for the phytoseiid mite. The term nutritional source should be understood to comprise any source of material that may serve as nutrition for the phytoseliid mite. Such a nutritional source may comprise an artificial diet, such as described in U.S. Pat. No. 6,129,935. However, as a nutritional source plant pollen or a prey are preferred. The prey may comprise a factitious host such as a species selected from the family of the Carpoglyphidae such as from the genus *Carpoglyphus*, preferably the species *Carpoglyphus lactis* or from other families or genera belonging to the Astigmata. By presenting an additional nutritional source, the phytoseiid mite is presented with a more diverse diet. It has been observed that combination of nutritional sources may lead to synergetic effects with respect to the predator's responses in terms of growth and/or reproduction.

According to a further aspect the present invention relates to a method for rearing the phytoseiid predatory mite species. The method comprises providing a composition according to the invention and allowing individuals of said phytoseiid predatory mite to prey on individuals of said factitious host population.

For an optimal development of the phytoseiid predatory mite, the composition is e.g. maintained at 18-35° C., preferably 20-30° C., more preferably 20-25° C., most preferably 22-25° C. Suitable relative humidity ranges are between 60-95%, preferably 70-90%. These temperature and relative humidity intervals are in general also suitable to maintain the factitious host species. It is preferred that the composition comprises a carrier which can provide a porous medium and a food substance for the factitious host species, and that the factitious host species is maintained as a three dimensional culture on the carrier. In such a three dimensional culture members of the factitious host species are free to move in three dimensions. In this way they may infest a larger volume of the carrier and utilise the food substance more optimally. Considering the size of the mobile stages of the phytoseiid predatory mite species relative to individuals of the factitious host, this organism will in general also infest the total volume of the carrier, when foraging for the factitious host. Preferably the three dimensional culture is obtained by providing the carrier in a three dimensional layer, i.e. a layer having three dimensions, of which two dimensions are larger then one dimension. Exemplary is a horizontal layer with a length and breadth in the order of meters and a certain thickness in the order of centimeters. A three dimensional layer is preferred because it will allow sufficient exchange of metabolic heat and gasses and will provide a larger production volume compared to a two dimensional layer.

According to a further aspect the invention is aimed to the use of an Astigmatid mite selected from the family of the Glycyphagidae as a factitious host for rearing a phytoseiid predatory mite.

The Astigmatid mite is preferably selected from the subfamily Ctenoglyphinae, such as from the genus *Diamesoglyphus* e.g. *D. intermedius* or from the genus *Ctenoglyphus*, e.g. *C. plumiger, C. canestrinii, C. palmifer*; the subfamily Glycyphaginae, such as from the genus *Blomia*, e.g. *B. freemani* or from the genus *Glycyphagus*, e.g. *G. ornatus, G. bicaudatus, G. privatus, G. domesticus*, or from the genus *Lepidoglyphus* e.g. *L. michaeli, L. fustifer, L. destructor*, or from the genus *Austroglycyphagus*, e.g. *A. geniculatus*; from the subfamily Aëroglyphinae, such as from the genus *Aëroglyphus*, e.g. *A. robustus*; from the subfamily Labidophorinae, such as from the genus *Gohieria*, e.g. *G. fusca*; or from the subfamily Nycteriglyphinae such as from the genus *Coproglyphus*, e.g. *C. Stammeri*, and more preferably is selected from the subfamily Glycyphaginae, and preferably is selected from the genus *Glycyphagus* or the genus *Lepidoglyphus*, most preferably selected from *G. domesticus* or *L. destructor*.

The phytoseiid predatory mite is preferably selected from:
the subfamily of the Amblyseiinae, such as from the Genus *Amblyseius*, e.g. *Amblyseius andersoni, Amblyseius swirskii, Amblyseius largoensis* or *Neoseiulus fallacis*, from the genus *Euseius* e.g. *Euseius finlandicus, Euseius hibisci, Euseius ovalis, Euseius victoriensis, Euseius stipulatus, Euseius scutalis, Euseius tularensis, Euseius addoensis, Euseius concordis, Euseius ho*, or *Euseius citri*, from the genus *Neoseiulus* e.g. *Neoseiulus barkeri, Neoseiulus californicus, Neoseiulus cucumeris, Neoseiulus longispinosus, Neoseiulus womersleyi, Neoseiulus idaeus, Neoseiulus anonymus* or *Neoseiulus fallacis*, from the genus *Typhlodromalus* e.g. *Typhlodromalus limonicus, Typhlodromalus aripo* or *Typhlodromalus peregrinus* from the genus *Typhlodromips* e.g. *Typhlodromips montdorensis;* the subfamily of the Typhlodrominae, such as from the genus *Galendromus* e.g. *Galendromus occidentalis*, from the genus *Typhlodromus* e.g. *Typhlodromus pyri, Typhlodromus doreenae* or *Typhlodromus athiasae.*

A selection from the subfamily of the Amblyseiinae is preferred.

According to a further aspect the invention relates to a rearing system for rearing the phytoseiid predatory mite.

The rearing system comprises a container holding the composition according to the invention. The container may be of any type which is suitable for restraining individuals of both populations. The rearing system may comprise means which facilitate exchange of metabolic gases and heat between it's interior and it's exterior such as ventilation holes. Such ventilation holes must not allow the substantial escape of individuals of the populations from the container. This can be effected by creating a barrier on or around the ventilation holes which prevents the substantial escape of mites from the container while facilitating exchange of gases and metabolic heat.

Due to predation of the phytoseiid predatory mites the number of individuals of the factitious host in the composition will decrease. If necessary, the factitious host may be replenished from a source comprising the factitious host, preferably together with the carrier and/or food substance for the factitious host.

The rearing system may be suitable for mass-rearing the phytoseiid mite species. Alternatively the rearing system may also be used for releasing the phytoseiid predatory mite in a crop. In this case it is preferred that the container can be rendered suitable to release mobile stages of the phytoseiid predatory mite at a certain moment. This can be effected by providing a closed opening in the container which can be opened. Alternatively or in combination therewith a relatively small releasing opening may be provided in the container, such that the number of phytoseiid mobile stages which leave the container in a given time interval is restricted. In this way the rearing system may function similar to the slow release or sustained release system as disclosed by Sampson, C., 1998 and in GB2393890.

In such a rearing system for releasing the phytoseiid predatory mite in a crop the container is preferably dimensioned such that it can be hung in the crop or placed at the basis of the crop. For hanging in the crop the container may be provided with hanging means, such as a cord or a hook.

According to a further aspect the invention is aimed at the use of the composition or the rearing system for controlling crop pests in a commercial crop.

Depending on the species of phytoseiid mite they can be used to control different pest species. The pest may be selected from, white flies, such as *Trialeurodes vaporariorum* or *Bemisia tabaci*; thrips, such as *Thrips tabaci* or *Frankliniella* spp., such as *Frankliniella occidentalis*; spider mites such as *Tetranychus urticae* or *Panonychus* spp.; tarsonemid mites such as *Polyphagotarsonemus latus*; eriophyid mites such as the tomato russet mite *Aculops lycopersici*; mealybug crawlers such as from the *Citrus* Mealybug *Planococcus citri*; scale crawlers such as from the California Red Scale *Aonidiella aurantii*.

The phytoseiid predatory mites *Amblyseius swirskii*, *Euseius ovalis* and *Euseius scutalis* have shown a good efficacy for controlling whiteflies and *thrips*. In the case of *Neoseiulus californicus*, *Neoseiulus fallacis*, *Neoseiulus womersleyi* the preferred target pests are spider mites belonging to the genus *Tetranychus* and *Panonychus*, tarsonemid mites such as the Broad Mite *Polyphagotarsonemus latus* and the Cyclamen Mite *Tarsonemus pallidus*. In the case of *Neoseiulus womersleyi* good efficacy has been shown against *thrips* such as *Franliniella occidentalis* and against eriophyid mites such as the Tomato Russet Mite *Aculops lycopersici*.

The crop may be selected from, but is not restricted to (greenhouse) vegetable crops such as tomatoes (*Lycopersicon esculentum*), peppers (*Capsicum annuum*), eggplants (*Solanum melogena*), Curcubits (*Cucurbitaceae*) such as cucumbers (*Cucumis sativa*), melons (*Cucumis melo*), watermelons (*Citrullus lanatus*); soft fruit (such as strawberries (*Fragaria x ananassa*), raspberries (*Rubus ideaus*)), (greenhouse) ornamental crops (such as roses, *gerberas, chrysanthemums*), tree crops such as *Citrus* spp., almonds, banana's or open field crops such as cotton, corn.

The invention further relates to a method for biological pest control in a crop comprising providing a composition according to the invention to said crop.

The pest may be selected similarly as in the use according to the invention.

In the method according to the invention the composition may be provided by applying an amount of said composition in the vicinity, such as on or at the basis of a number of crop plants. The composition may be provided to the crop plant simply by spreading it on the crop plant or at the basis of the crop plant as is common practice for employing predatory mite compositions for augmentative biological pest control. The amount of the composition which may be provided to each individual crop plant by way of spreading may range from 1-20 ml such as 1-10 ml, preferably 2-5 ml when applying at the basis of the crop plants and 0.1-5 ml when applying on the leaf canopy of the plants.

Alternatively the composition may be provided to the number of crop plants in the rearing system according to the invention which is suitable for releasing the phytoseiid predatory mite in a crop. The rearing system may be placed in the vicinity, such as in or at the basis, of a number of crop plants.

In the method for biological pest control according to the invention it may not be necessary to provide the composition to all crop plants. As commercial crops are normally densely cultivated. The phytoseiid predatory mites may spread from one crop plant to another. The number of crop plants which must be provided with the composition according to the invention in order to provide sufficient crop protection may depend on the specific circumstances and can be easily determined by the skilled person based on his experience in the field. Usually the number of phytoseiid predatory mites released per hectare is more determining. This number may range from 1000-4 million per hectare, typically 100.000-1 million or 50.000-500.000 per hectare. These numbers may be released once or multiple times per growing season, depending on climatic conditions, pest pressure and usage of harmful pesticides.

In a further preferred embodiment of the method for biological pest control according to the invention the crop is selected as described in relation to the use of the composition.

The invention will now be further described with reference to the following examples, which show non-limiting embodiments of different aspects of the invention.

Experiment 1 Oviposition Test of *N. fallacis* on *L. destructor*.
Material and Methods At the beginning of the experiment the *N. fallacis* adults were taken from an *N. fallacis* mass-culture on the food source *L. destructor*, which was started a few weeks earlier. 20 young adult females and 8 males were picked up from this mass-culture and transferred to four freshly prepared rearing containers. 5 females and 2 males of *N. fallacis* were placed in each one. In all of them as a food source was placed an ample amount of *L. destructor*.

Once the four test cultures were prepared, they were located in a climate room under controlled temperature (25° C.) and humidity (75%) conditions. After two or three days in these conditions, they were taken out. Four new rearing containers, similar to the previous ones, were prepared to transfer the same 5 females and 2 males previously used.

Ample amount of *L. destructor* as a food source were added to each test culture as in the previous step. After transferring the males and females, the number of eggs was counted in the rearing containers from which they were transferred.

The old rearing systems were conserved in the climate room during two or three days for a second counting in order to detect some possible hidden offspring, after which they were destroyed. Similar to the old rearing systems, the new ones were also maintained to repeat the same procedure. Every day the residual amount of *L. destructor* in each rearing container was checked. If necessary a sufficient amount was added.

Every two or three days data were obtained by evaluating the number of offsprings of both the new rearing (first counting) and the old one (second counting). Based on the number of females and on the total amount of offspring which was found on each rearing container, the mean number of eggs laid per female per day was obtained.

Results

When comparing the evolution of the number of eggs laid per female during the total experiment (making one counting assessment each 2-3 days), the mean ranges from 1.80 to 2.63 eggs/female/day.

For the whole period, the general mean is 2.14 eggs per female per day. The total amount of eggs laid per female is about 23 over a 11 days period. Comparing the mean number of eggs laid per female per day for the first, second, third and fourth independent rearing container, these are 2.07, 2.09, 2.42 and 2.00, respectively. The experimental data is presented in table 1 below.

TABLE 1

Food source: all stages of *L. destructor*.
Data of the mean number of eggs laid per *N. fallacis* female per day for the 4 independent rearing systems and for the global experiment.

| Exp. | Day | Females | Total offspring | egg/day/ female | Mean eggs/day/female |
|---|---|---|---|---|---|
| 1 | 2 | 5 | 18 | 1.80 | 2.07 |
|   | 4 | 5 | 20 | 2.00 |   |
|   | 7 | 5 | 29 | 1.93 |   |
|   | 9 | 5 | 24 | 2.40 |   |
|   | 11 | 5 | 22 | 2.20 |   |
| 2 | 2 | 5 | 19 | 1.90 | 2.09 |
|   | 4 | 5 | 18 | 1.80 |   |
|   | 7 | 5 | 32 | 2.13 |   |
|   | 9 | 5 | 25 | 2.50 |   |
|   | 11 | 5 | 21 | 2.10 |   |
| 3 | 2 | 5 | 18 | 1.80 | 2.42 |
|   | 4 | 5 | 23 | 2.30 |   |
|   | 7 | 5 | 34 | 2.27 |   |
|   | 9 | 5 | 31 | 3.10 |   |
|   | 11 | 4 | 21 | 2.63 |   |
| 4 | 2 | 5 | 18 | 1.80 | 2.00 |
|   | 4 | 5 | 18 | 1.80 |   |
|   | 7 | 5 | 33 | 2.20 |   |
|   | 9 | 5 | 23 | 2.30 |   |
|   | 11 | 5 | 19 | 1.90 |   |

| day | Period | Females | Offspring | eggs/day/ female | Mean eggs/day/females |
|---|---|---|---|---|---|
| 2 | 0-2 days | 20 | 73 | 1.83 | 2.14 |
| 4 | 3-4 days | 20 | 79 | 1.98 |   |
| 7 | 5-7 days | 20 | 128 | 2.13 |   |
| 9 | 8-9 days | 20 | 103 | 2.58 |   |
| 11 | 10-11 days | 19 | 83 | 2.18 |   |

Experiment 2: Oviposition Test of *N. californicus* on *L. destructor*

In essence similar to the method described in experiment 1 oviposition test were performed for *N. fallacis*.

These experiments differed as follows:
  Instead of 4 subexperiments with 5 female *A. fallacis*, 4 subexperiments with 4 female *N. californicus* were conducted.
  The testing period with *N. californicus* was 14 days in stead of 11 days.

Results

When comparing the evolution of the number of eggs laid per female during the total experiment (making one counting assessment each 2-3 days), the mean ranges from 1.25 to 3.33 eggs/female/day.

For the whole period, the general mean is 2.27 eggs per female per day. The total amount of eggs laid per female is about 31 over a 14 days period. Comparing the mean number of eggs laid per female per day for the first, second, third and fourth independent rearing container, these are 2.50, 2.44, 2.49 and 1.70, respectively. The experimental data is presented in table 2 below.

TABLE 2

Food source: all stages of *L. destructor*.
Data of the mean number of eggs laid per *N. californicus* female per day for the 4 independent rearing systems and for the global experiment.

| Exp. | Day | Females | Total offspring | egg/day/ female | Mean eggs/day/female |
|---|---|---|---|---|---|
| 1 | 2 | 4 | 23 | 2.88 | 2.50 |
|   | 5 | 4 | 35 | 2.92 |   |
|   | 7 | 4 | 18 | 2.25 |   |
|   | 9 | 4 | 19 | 2.38 |   |
|   | 12 | 4 | 25 | 2.08 |   |
|   | 14 | 4 | 20 | 2.50 |   |
| 2 | 2 | 4 | 21 | 2.63 | 2.44 |
|   | 5 | 4 | 29 | 2.42 |   |
|   | 7 | 4 | 20 | 2.50 |   |
|   | 9 | 4 | 15 | 1.88 |   |
|   | 12 | 4 | 29 | 2.42 |   |
|   | 14 | 3 | 17 | 2.83 |   |
| 3 | 2 | 4 | 20 | 2.50 | 2.49 |
|   | 5 | 3 | 30 | 3.33 |   |
|   | 7 | 3 | 14 | 2.33 |   |
|   | 9 | 3 | 15 | 2.50 |   |
|   | 12 | 3 | 16 | 1.78 |   |
|   | 14 | 3 | 15 | 2.50 |   |
| 4 | 2 | 4 | 14 | 1.75 | 1.70 |
|   | 5 | 4 | 25 | 2.08 |   |
|   | 7 | 4 | 13 | 1.63 |   |
|   | 9 | 4 | 14 | 1.75 |   |
|   | 12 | 4 | 15 | 1.25 |   |
|   | 14 | 4 | 14 | 1.75 |   |

| day | Period | Females | Offspring | eggs/day/ female | Mean eggs/day/females |
|---|---|---|---|---|---|
| 2 | 0-2 days | 16 | 78 | 2.44 | 2.27 |
| 5 | 3-5 days | 15 | 119 | 2.64 |   |
| 7 | 6-7 days | 15 | 65 | 2.17 |   |
| 9 | 8-9 days | 15 | 63 | 2.10 |   |
| 12 | 10-12 days | 15 | 85 | 1.89 |   |
| 14 | 13-14 days | 14 | 66 | 2.36 |   |

Biological Parameters of *N. californicus* in the First 3 Generation and after Adaptation on *Lepidoglyphus destructor*

Experimental Procedures—

*N. californicus* was collected from mass rearing on *Quercus* spp. pollen maintained at about 25° C., RH>80% and 16L: 8D. The experiment was performed at the same conditions. The rearing units (RU) were a plastic arena (diameter about cm 4.5), surrounded by wetted cotton and partially covered. Young ovipositing females of *N. californicus* were put in the RU and fed with *L. destructor*. The prey (all stages) was added to arenas in such a way as to daily maintain an amount of prey higher than the phytoseiid consumption.

The eggs of *N. californicus* oviposited in the first 2 days were removed. The egg laid the successive two days were daily collected; some of them were placed on new RU in small groups to calculate mortality and sex ratio, the others were singly isolated to calculate development times and egg-to-egg-time. From the progeny newly virgin females were confined with a mature male and the each couple daily followed for then day to register oviposition and female longevity on the period.

The coeval eggs obtained were collected and used to start the second generation on *L. destructor*: the procedure used for the first generation was repeated for the second and third generation.

The performance of *N. californicus* on *L. destructor* was evaluated on the first-third generations and on an adapted strain (more than one year and half feeding on *L. destructor*)

TABLE 3

Biological parameters of *N. californicus* on *L. destructor* (25° C. ± 2° C., RH >80%, photoperiod 16L: 8D)

| | generations | | | |
|---|---|---|---|---|
| | 1st | 2nd | 3th | Nth |
| egg-to-egg time (days) | 8.6 ± 0.96 a<br>n = 36 | 9.9 ± 1.27 b<br>n = 25 | 9.5 ± 1.20 b<br>n = 33 | 8.6 ± 1.10 a<br>n = 34 |
| juvenile mortality (%) | 0.39 a<br>n = 259 | 0.65 a<br>n = 159 | 1.60 a<br>n = 187 | 1.67 a<br>n = 180 |
| sex ratio (females %) | 66.67 a<br>n = 258 | 63.64 a<br>n = 154 | 58.70 ab<br>n = 184 | 55.37 b<br>n = 177 |
| escape rate (%) | 13.71<br>n = 300 | 21.43<br>n = 197 | 25.51<br>n = 250 | 30.32<br>n = 254 |
| eggs/female/day (10 day period) | 2.29 ± 0.0.43 a<br>n = 33 | 2.03 ± 0.45 b<br>n = 32 | 2.75 ± 0.49 c<br>n = 31 | 2.15 ± 0.50 ab<br>n = 26 |

Demographic Parameters of *N. californicus* on *L. destructor*

Data obtained on *L. destructor* were used to calculate $r_g$ and $r_m$. The values obtained were summarized in the Table 4.

TABLE 4

Net reproductive rate ($r_g$) and estimate intrinsic growth rate ($r_m$) of *N. californicus* on *L. destructor* in the different generation at 25° C. and RH ≥80%

| | $r_g$ calculated (day$^{-1}$) | $r_m$ estimated (day$^{-1}$) |
|---|---|---|
| 1st generation | 0.222 | 0.244 |
| 2nd generation | 0.205 | 0.225 |
| 3th generation | 0.199 | 0.218 |
| nth generation | 0.203 | 0.223 |

REFERENCES

Athias-Henriot, C. (1962) *Amblyseius swirskii*, un nouveau phytoseiide voisin d'A. andersoni (Acariens anactinotriches). Annales de l'Ecole Nationale d'Agriculture d'Alger, Algeria, 3, 1-7.

Beglyarov et al., 1990, Flour mite for mass breeding of phytoseiids, Zashchita-Rastenii, no. 10, pp 25. Bennison, J. A. and Jacobson, R., 1991, Integrated control of *Frankliniella occidentalis* (Pergande) in UK cucumber crops—evaluation of a controlled release system of introducing *Amblyseius cucumeris*, Med. Fac. Landbouww. Rijksuniv. Gent, 56/2a, pp 251-255.

Bolckmans, K. & Moerman, M. 2004, Nieuwe roofmijt verandert bestrijding in paprika. Groenten & Fruit 41: 24-25

Castagnoli, M., 1989, Biologia e prospettive di allevamento massale di *Amblyseius cucumeris* (Oud.) (Acarina: Pyroglyphidae) com preda.

Castagnoli, M. and Simoni, S., 1999, Effect of long-term feeding history on functional and numerical response of *Neoseiulus californicus* (Acari: Phytoseiidae), Experimental & Applied Acarology, 23, pp 217-234.

Castagnoli M., Simoni S., Biliotti N., 1999, Mass-rearing of *Amblyseius californicus* on two alternative food source—In: J. Bruin, L. P. S. van der Geest and M. W. Sabelis (eds), Ecology and Evolution of the Acari, Kluwer Acad, Publ., Dordrecht, The Nederlands, pp. 425-431.

Chant, D. A., and J. A., McMurtry, 2004, A review of the subfamily Amblyseiinae Muma (Acari: Phytoseiidae): Part III. The tribe Amblyseiini wainstein, subtribe Amblyseiina N. subtribe. Internat. J. Acarol., vol. 30, Nr. 3, p. 171-228.

Chmielewski, W., 1971(a), Wyniki badan morfologicznych, biologicznych i ekologicznych nad roztoczkiem suszowym, *Carpoglyphus lactis* (L.) (The results of investigations on the morphology, biology and ecology of the dried-fruit mite, *Carpoglyphus lactis* (L.)), Prace-Naukowe-Instytutu-Ochrony-Roslin. 1971, publ. 1972, 13: 1, 87-106.

Chmielewski, W., 1971(b), Morfologia, biologia i ekologia *Carpoglyphus lactis* (L., 1758) (Glycyphagidae, Acarina) (The morphology, biology and ecology of *Carpoglyphus lactis* (L., 1758) (Glycyphagidae, Acarina)), Prace-Naukowe-Instytutu-Ochrony-Roslin. 1971, publ. 1972, 13: 2, 63-166.

De Moraes, G. J., McMurtry, J. A., Denmark, H. A. & Cameos, C. B., 2004. A revised catalog of the mite family Phytoseiidae. Magnolia Press Auckland New Zealand 494 pp.

Dyadechko, N. P. & Chizhik, 1972 (On the multiplication of yphlodromus) (in Russian). Zashch. Rast. 17(2):22.

Glasshouse Crops Research Institute, UK. 1976, Biological Pest Control. Rearing parasites and predators. Grow. Bull. Glasshouse Crops Res. Inst.: 23 pp.

Hansen, L. S. and Geyti. J., 1985, Possibilities and limitation of the use of *Amblyseius* McKenziei Sch. & Pr. for biological control of *thrips* (*Thrips tabaci* Lind.) On glasshouse corps of cucumber, Department of Zoology, Danish Research Centre for Plant Protection, Lyngby, Denmark, pp 145-150.

Hendrickson, R. M., Jr., 1980, Continuous production of predacious mites in the greenhouse. J.N.Y. Entomol. Soc. 88(4): 252-256.

Hughes, A. M., 1977, The mites of stored food and houses. Ministry of Agriculture, Fisheries and Food, Technical Bulletin No. 9: pp 133-186

Hussey, N. W. and N. E. A. Scopes, 1985, Biological Pest Control: the Glasshouse Experience. Poole, UK.: Blandford Press (Ithaca, N.Y.: Cornell University Press)

Jacobson, R. J., 1995, Integrated pest management in cucumbers—prevention of establishment of *Frankliniella occidentalis* (Pergande), Med. Fac. Landbouww. Univ. Gent, 60/3a, pp 857-863.

Karg et al., 1987, Advantages of oligophagous predatory mites for biological control, Institute of Plant Protection Klenmachnow, pp 66-73.

Karg et al., 1989, Fortschritte bei der Anwendung von Raubmilben zur biologischen Schädlingsbekämpfung in Gewächshäusern, Gartenbau, 36, pp 44-46.

Karg, W., 1989, Die ökologische Differenzierung der Faubmilbarten der Überfamilie Phytoseiidea KARG (Acarina, Parasitiformes), Zool. Jb. Syst. 116, pp 31-46.

Messelink, G. & Steenpaal, S. 2003, Nieuwe roofmijten tegen trips in komkommer. Groenten & Fruit 43: 34-35.

Messelink, G. 2004, Nieuwe roofmijt wint met overmacht in komkommer. Groenten & Fruit 35: 22-23.

Messelink, G. & Pijnakker, J. 2004, Roofmijten bestrijden wittevlieg. Vakblad voor de Bloemisterij 43: 62.

Messelink, G. & Steenpaal, S. 2004, Roofmijt nu ook kaswittevlieg de baas. Groenten & Fruit 45: 26-27.

McMurtry, J. A. and CroftB. A., 1997, Life-styles of phytoseiid mites and their role in biological control, Annual Review of Entomology, Vol. 42: 291-321.

Nomikou, M., Janssen, A., Schraag, R. and Sabelis, M. W., 2001, Phytoseiid predators as biological control agents for *Bemisia tabaci*. Exp. Appl. Acarol. 25: 270-290

Parkinson, C. L., 1992, "Culturing free-living astigmatid mites." Arachnida: Proceedings of a one day symposium on spiders and their allies held on Saturday 21 Nov. 1987 at the Zoological Society of London, eds. Cooper, J. E., Pearce-Kelly, P, Williams, D. L., p. 62-70.

Ramakers, P. M. J. and Van Lieburg, M. J., 1982, Start of commercial production and introduction of *Amblyseius mckenzei* Sch. & Pr. (Acarina: Phytoseiidae) for the control of *Thrips tabaci* Lind. (*Thysanoptera: Thripidae*) in glasshouses, Med. Fac. Landbouww. Rijksuniv. Gent, 47/2, pp 541-545.

Ramakers, P. M. J., 1989, Large scale introductions of Phytoseiid predators to control *thrips* on cucumber, Med. Fac. Landbouww. Rijksuniv. Gent, 54/3a, pp 923-929.

Ramakers, P. M. J. and Voet, S. J. P., 1996, Introduction of *Amblyseius degenerans* for *thrips* control in sweet peppers with potted castor beans as banker plants. IOBC/WPRS working group on integrated control in glasshouses 19(1): 127-130.

Rasmy et al., 1987, A new diet for reproduction of two predaceous mites *Amblyseius gossipi* and *Agistemus exsertus* (Acari: Phytoseiidae, Stigmaeidae), Entomophaga 32(3), pp 277-280.

Romeih, A. H. M., El-Saidy, E. M. A. and El Arnaouty, S. A., 2004, Suitability Of Two Lepidopteran Eggs As Alternative Preys For Rearing Some Predatory Mites. The first Arab Conference of Applied Biological Pest Control, Cairo, Egypt, 5-7 Apr. 2004.

Swirski, E., Amitai, S. and Dorzia, N., 1967, Laboratory studies on the feeding, development and oviposition of the predaceous mite *Amblyseius rubini* Swirksi and Amitai an *Amblyseius swirskii* Athias-Henriot (Acarina:Phytoseiidae) on various kinds of food substances. Israel J. Agric. Res. 17:101-119

Sampson, C., 1998, The commercial development of an *Amblyseius cucumeris* controlled release method for the control of *Frankliniella occidentalis* in protected crops, The 1998 Brighton conference—Pests & Diseases, 5B-4, pp 409-416.

Solomon, M. E. and Cunnington, A. M., 1963, Rearing acaroid mites, Agricultural Research Council, Pest Infestation Laboratory, Slough, England, pp 399-403.

Teich, Y. 1966, Mites of the family of Phytoseiidae as predators of the tobacco whitefly, *Bemisia tabaci* Gennadius. Israel J. Agric. Res. 16: 141-142.

Wei-Lan Ma and J. E. Laing, 1973, Biology—of *Amblyseius* (*Neoseiulus*) *californicus*, Entomophaga, 47-60.

The invention claimed is:

1. A composition comprising:
a rearing population of a phytoseiid predatory mite species selected from the group consisting of the subfamily of the Ablyseiinae and the subfamily of the Typhlodrominae, wherein mites from the subfamily of the Amblyseiinae are selected from the group consisting of a mite species from the genus *Amblyseius*, a mite species from the genus *Euseius*, the mite species *Neoseiulus califomicus*, the mite species *Neoseiulus fallacis*, a mite species from the genus *Typhlodromalus*, and a mite species from the genus *Typhlodromips*,
a factitious host population that comprises at least one species selected from the family of the Glycyiphagidae, and optionally a carrier for individuals of said populations.

2. The composition according to claim 1, further comprising a food substance suitable for said factitious host population.

3. The composition according to claim 1, wherein the factitious host population is a rearing population.

4. The composition according to claim 1, wherein the number of individuals of the phytoseiid predatory mite species relative to the number of individuals of the factitious host is from about 100:1 to 1:20.

5. The composition according to claim 1, wherein the factitious host species is selected from a subfamily selected from the group consisting of: the subfamily Ctenoglyphinae; the subfamily Glycyphaginae; the subfamily Aëroglyphinae; the subfamily Labidophorinae; and the subfamily Nycteriglyphinae.

6. The composition according to claim 5, wherein the factitious host species is selected from the subfamily Glycyphaginae.

7. The composition according to claim 6, wherein the factitious host species is selected from the genus *Glycyphagus* or the genus *Lepidoglyphus*.

8. The composition according to claim 7, wherein the factitious host species is selected from *G. domesticus* or *L. destructor*.

9. The composition according to claim 1, further comprising a further nutritional source for the phytoseiid mite.

10. The composition according to claim 9, wherein the nutritional source is pollen or a prey.

11. The composition according to claim 10, wherein the prey comprises a factitious host selected from the family of the Carpoglyphidae.

12. The composition according to claim 1, wherein the phytoseiid mite is not *Amblyseius swirskii*.

13. The composition according to claim 1, wherein the phytoseiid predatory mite species is a species selected from the group consisting of: *Amblyseius andersoni*, *Amblyseius swirskii*, *Amblyseius largoensis*, *Euseius finlandicus*, *Euseius hibisci*, *Euseius ovalis*, *Euseius victoriensis*, *Euseius stipulatus*, *Euseius scutalis*, *Euseius tularensis*, *Euseius addoensis*, *Euseius concordis*, *Euseius ho* or *Euseius citri*, *Neoseiulus californicus*, *Neoseiulus fallacis*, *Typhlodromalus limonicus*, *Typhlodromalus aripo*, *Typhlodromalus peregrinus*, *Typhlo-*

*dromips montdorensis, Galendromus occidentalis, Typhlodromus pyri, Typhlodromus doreenae* and *Typhlodromus athiasae*.

14. The composition according to claim 1, wherein the phytoseiid predatory mite species is selected from the genus *Galendromus* and the genus *Typhlodromus*.

15. The composition according to claim 1, wherein the rearing population of a phytoseiid predatory mite species has a number of individuals that can grow by sexual reproduction by 50% or more in 7 days (T=25° C.; RH=80% feeding ad libidum).

16. Method for rearing a phytoseiid predatory mite comprising:
providing a composition according to claim 1,
allowing individuals of said phytoseiid predatory mite to prey on individuals of said factitious host population.

17. Method according to claim 16, wherein the composition is maintained at 18-35° C. and/or 60-95% relative humidity.

18. Method according to claim 16, wherein said composition comprises a carrier and a suitable food substance and the factitious host population is maintained as a three-dimensional culture on the carrier.

19. Rearing system for rearing a phytoseiid predatory mite, which system comprises a container holding the composition according to claim 1.

20. Rearing system according to claim 19, wherein said container comprises an exit for at least one mobile life stage of the phytoseiid mite.

21. Rearing system according to claim 20, wherein said exit is suitable for providing a sustained release of said at least one mobile life stage.

22. Method for biological pest control in a crop comprising providing a composition according to claim 1 to said crop.

23. Method according to claim 22 wherein the pest is selected from white flies, *thrips*, spider mites, tarsonemid mites, eriophyid mites, mealybug crawlers, and scale crawlers.

24. Method according to claim 22, wherein the composition is provided by applying an amount of said composition to a number of crop plants.

25. Method according to claim 24, wherein the amount is from 1-10 ml, preferably 2-5 ml.

26. Method according to claim 22, wherein the composition is provided in the rearing system according to claim 20, by placing said rearing system among a number of crop plants.

27. Method according to claim 22, wherein the crop is selected from greenhouse vegetable crops, greenhouse ornamental crops, tree crops or open field crops.

* * * * *